United States Patent
Freiin von Kapri et al.

(10) Patent No.: US 12,175,018 B2
(45) Date of Patent: Dec. 24, 2024

(54) METHODS FOR DETERMINING IF TELEOPERATION SHOULD BE DISENGAGED BASED ON THE USER'S GAZE

(71) Applicant: Verb Surgical Inc., Santa Clara, CA (US)

(72) Inventors: Anette Lia Freiin von Kapri, Mountain View, CA (US); Denise Ann Miller, Scotts Valley, CA (US); Paolo Invernizzi, Milan (IT); Joan Savall, Palo Alto, CA (US); John Magnasco, San Jose, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/599,778

(22) Filed: Mar. 8, 2024

(65) Prior Publication Data
US 2024/0288936 A1    Aug. 29, 2024

Related U.S. Application Data

(63) Continuation of application No. 17/527,502, filed on Nov. 16, 2021, now Pat. No. 11,960,645, which is a
(Continued)

(51) Int. Cl.
| | |
|---|---|
| *G06F 3/01* | (2006.01) |
| *A61B 34/00* | (2016.01) |
| *A61B 34/35* | (2016.01) |

(52) U.S. Cl.
CPC .............. *G06F 3/013* (2013.01); *A61B 34/25* (2016.02); *A61B 34/35* (2016.02)

(58) Field of Classification Search
CPC ......... G06F 3/013; A61B 34/25; A61B 34/35; A61B 34/37; A61B 2017/00216; A61B 34/30
(Continued)

(56) References Cited

U.S. PATENT DOCUMENTS

| | | |
|---|---|---|
| 7,865,266 B2 | 1/2011 | Moll et al. |
| 8,831,782 B2 | 9/2014 | Itkowitz |

(Continued)

FOREIGN PATENT DOCUMENTS

| | | |
|---|---|---|
| CN | 101193603 A | 6/2008 |
| CN | 102958464 A | 3/2013 |

(Continued)

OTHER PUBLICATIONS

Camarillo et al., "Robotic Technology in Surgery: Past, Present and Future", Departments of Mechanical Engineering, Computer Science and Surgery, Stanford University, Stanford, CA, 2004, 43 pages.
(Continued)

*Primary Examiner* — John W Miller
*Assistant Examiner* — Omer Khalid
(74) *Attorney, Agent, or Firm* — Aikin & Gallant, LLP

(57) ABSTRACT

A method for disengaging a surgical instrument of a surgical robotic system comprising receiving a gaze input from an eye tracker; determining, by one or more processors, whether the gaze input indicates the gaze of the user is outside or inside of the display; in response to determining the gaze input indicates the gaze of the user is outside of the display, determining an amount of time the gaze of the user is outside of the display; in response to determining the gaze of the user is outside of the display for less than a maximum amount of time, pause the surgical robotic system from a teleoperation mode; and in response to determining the gaze
(Continued)

of the user is outside of the display for more than the maximum amount of time, disengage the surgical robotic system from the teleoperation mode.

19 Claims, 6 Drawing Sheets

Related U.S. Application Data continuation of application No. 16/415,974, filed on May 17, 2019, now Pat. No. 11,204,640.

(58) Field of Classification Search
USPC .......................................................... 345/156
See application file for complete search history.

(56) References Cited

U.S. PATENT DOCUMENTS

| | | |
|---|---|---|
| 9,314,306 B2 | 4/2016 | Yu |
| 9,360,934 B2 | 6/2016 | Ruiz et al. |
| 9,699,445 B2 | 7/2017 | Hoffman et al. |
| 9,901,402 B2 | 2/2018 | Itkowitz et al. |
| 9,925,662 B1 | 3/2018 | Jules et al. |
| 10,251,713 B2 | 4/2019 | Ruiz et al. |
| 10,895,757 B2 | 1/2021 | Fuerst et al. |
| 10,980,610 B2 | 4/2021 | Rosenberg et al. |
| 11,204,640 B2 | 12/2021 | Freiin et al. |
| 11,224,489 B2 | 1/2022 | Ruiz et al. |
| 11,333,899 B2 | 5/2022 | Fuerst et al. |
| 11,337,767 B2 | 5/2022 | Savall et al. |
| 11,478,318 B2 | 10/2022 | Cone et al. |
| 2008/0181452 A1 | 7/2008 | Kwon et al. |
| 2009/0315827 A1 | 12/2009 | Elvesjoe et al. |
| 2011/0118748 A1 | 5/2011 | Itkowitz |
| 2012/0071892 A1 | 3/2012 | Itkowitz et al. |
| 2012/0078080 A1 | 3/2012 | Foley et al. |
| 2014/0024889 A1 | 1/2014 | Xiaoli |
| 2015/0080909 A1 | 3/2015 | Itkowitz et al. |
| 2015/0314447 A1 | 11/2015 | Zhang et al. |
| 2016/0242860 A1 | 8/2016 | Diolaiti et al. |
| 2016/0346053 A1 | 12/2016 | Beira |
| 2016/0361125 A1 | 12/2016 | Balicki et al. |
| 2017/0172675 A1 | 6/2017 | Jarc et al. |
| 2017/0180720 A1 | 6/2017 | Jarc |
| 2018/0016110 A1 | 1/2018 | Nobe et al. |
| 2018/0036088 A1 | 2/2018 | Kilroy et al. |
| 2018/0078034 A1 | 3/2018 | Savall et al. |
| 2018/0078319 A1 | 3/2018 | Nobles et al. |
| 2018/0092706 A1 | 4/2018 | Anderson et al. |
| 2018/0161108 A1 | 6/2018 | Savall et al. |
| 2018/0280099 A1 | 10/2018 | Cone et al. |
| 2018/0364810 A1 | 12/2018 | Parshionikar |
| 2019/0076199 A1 | 3/2019 | Kline et al. |
| 2019/0231456 A1 | 8/2019 | Ruiz et al. |
| 2019/0298481 A1 | 10/2019 | Rosenberg et al. |
| 2019/0328473 A1 | 10/2019 | Chassot et al. |
| 2020/0015918 A1* | 1/2020 | Payyavula ............. B25J 9/1689 |
| 2020/0038124 A1 | 2/2020 | Lin et al. |
| 2020/0093367 A1 | 3/2020 | Dory et al. |
| 2020/0163732 A1 | 5/2020 | Hasser et al. |
| 2020/0222138 A1 | 7/2020 | Diolaiti |
| 2020/0315721 A1 | 10/2020 | Rabindran et al. |
| 2020/0360097 A1 | 11/2020 | Dimaio et al. |
| 2020/0363868 A1 | 11/2020 | Freiin et al. |
| 2020/0390510 A1 | 12/2020 | Thompson et al. |
| 2021/0088807 A1 | 3/2021 | Fuerst et al. |
| 2021/0145526 A1 | 5/2021 | Robinson et al. |
| 2021/0145532 A1 | 5/2021 | Tucker et al. |
| 2022/0179483 A1 | 6/2022 | Freiin et al. |
| 2024/0024051 A1 | 1/2024 | Tokarchuk et al. |

FOREIGN PATENT DOCUMENTS

| | | |
|---|---|---|
| CN | 105877846 A | 8/2016 |
| CN | 106659540 A | 5/2017 |
| CN | 107847283 A | 3/2018 |
| CN | 107847284 A | 3/2018 |
| CN | 108472097 A | 8/2018 |
| CN | 109475387 A | 3/2019 |
| EP | 3395251 A1 | 10/2018 |
| JP | 2007-290096 A | 11/2007 |
| KR | 10-1802464 B1 | 11/2017 |
| WO | 2018/057814 A1 | 3/2018 |
| WO | 2018/162921 A1 | 9/2018 |
| WO | 2018/165047 A1 | 9/2018 |
| WO | 2018/195319 A1 | 10/2018 |
| WO | 2018/217444 A2 | 11/2018 |

OTHER PUBLICATIONS

Extended European Search Report for European Application No. 18945174.3 mailed Oct. 27, 2022, 9 pages.
Final Office Action of the U.S. Patent Office dated Feb. 22, 2022 for related U.S. Appl. No. 16/236,163.
Final Office Action of the U.S. Patent Office dated May 25, 2021 for related U.S. Appl. No. 16/415,974.
Final Office Action of the U.S. Patent Office dated May 3, 2021 for related U.S. Appl. No. 16/236,163.
First Office Action for Chinese Application No. 201980096511.9, mailed Oct. 28, 2023.
International Preliminary Report on Patenlability for International Application No. PCT/US2019/034721 mailed Dec. 2, 2021, 9 pages.
International Preliminary Report on Patentability for International Application No. PCT/US2019/034722 mailed Dec. 2, 2021, 9 pages.
International Preliminary Report on Patentability for International Application No. PCT/US2019/068221 mailed Jul. 8, 2021, 8 pages.
International Preliminary Report on Patentability for International Application No. PCT/US2019/068221 mailed Jun. 16, 2021, 8 pages.
International Search Report & Written Opinion of the PCT Patent Office dated Feb. 3, 2020 for related PCT Patent Application. No. PCT/US2019/034721.
International Search Report & Written Opinion of the PCT Patent Office dated Feb. 6, 2020 for related PCT Patent Application. No. PCT/US2019/034722.
International Search Report and Written Opinion dated Sep. 23, 2019 for related PCT Appln. No. PCT/US2018/068221 18 Pages.
International Search Report and Written Opinion of the PCT Patent Office dated Sep. 23, 2019 for related PCT Patent Application No. PCT/US2018/068221.
Jack Lloyd, How to Sync a PS3 Controller. Sep. 18, 2018, Accessed through: https://www.wikihow.com/Sync-a-PS3-Controller (Year: 2018).
Latif et al., "Teleoperation through Eye Gaze (TeleGaze): A Multimodal Approach", Published in: 2009 IEEE International Conference on Robotics and Biomimetics (ROBIO), Dec. 2009, 6 Pages.
Non-Final of the U.S. Patent Office dated Jan. 12, 2021 for related U.S. Appl. No. 16/415,974.
Non-Final Office Action of the U.S. Patent Office dated Dec. 14, 2020 for related U.S. Appl. No. 16/236,163.
Non-Final Office Action of the U.S. Patent Office dated Oct. 6, 2021 for related U.S. Appl. No. 16/415,992.
Non-Final Office Action of the U.S. Patent Office dated Oct. 7, 2021 for related U.S. Appl. No. 16/236,163.
Notice of Allowance of the U.S. Patent Office dated Aug. 13, 2021 for related U.S. Appl. No. 16/415,974.
Notice of Allowance of the U.S. Patent Office dated Jan. 26, 2022 for related U.S. Appl. No. 16/415,992, mailed on Jan. 26, 2022, 8 pages.
Notice of Allowance of the U.S. Patent Office dated Jun. 10, 2022 for related U.S. Appl. No. 16/236,163.
Notice of Allowance of the U.S. Patent Office dated Mar. 18, 2022 for related U.S. Appl. No. 16/415,992.
Notice of Allowance of the USPTO mailed Jan. 26, 2022 for related U.S. Appl. No. 16/415,792.

(56) References Cited

OTHER PUBLICATIONS

Office Action received for Chinese Patent Application No. 201880100540.3, mailed on Nov. 27, 2023, 27 pages (16 pages of English Translation and 11 pages of Original Document).
Office Action received for Chinese Patent Application No. 201980096510.4, mailed on Dec. 26, 2023, 27 pages (14 pages of English Translation and 13 pages of Original Document).

* cited by examiner

METHODS FOR DETERMINING IF TELEOPERATION SHOULD BE DISENGAGED BASED ON THE USER'S GAZE

CROSS-REFERENCE TO RELATED APPLICATIONS

This application is a continuation of U.S. patent application Ser. No. 17/527,502, filed Nov. 16, 2021, which is a continuation of U.S. patent application Ser. No. 16/415,974, filed May 17, 2019, now U.S. Pat. No. 11,204,640, issued Dec. 21, 2021, which are incorporated herein in their entirety.

BACKGROUND

Field

Embodiments related surgical robotic systems are disclosed. More particularly, embodiments related to surgical robotic systems and corresponding methods for determining if a teleoperation mode of the surgical robotic system should be disengaged based on a user's gaze, are disclosed.

Background

Endoscopic surgery involves looking into a patient's body and performing surgery inside the body using endoscopes and other surgical tools. For example, laparoscopic surgery can use a laparoscope to access and view an abdominal cavity. Endoscopic surgery can be performed using manual tools and/or a surgical robotic system having robotically-assisted tools.

A surgical robotic system may be remotely operated by a surgeon to command a robotically-assisted tool located at an operating table. Such operation of a robotically-assisted tool remotely by a surgeon may be commonly referred to as teleoperation or a teleoperation mode. For example, the surgeon may use a computer console located in the operating room, or it may be located in a different city, to command a robot to manipulate the surgical tool mounted on the operating table. The robotically-controlled surgical tool can be an endoscope mounted on a surgical robotic arm. Accordingly, the surgical robotic system may be used by the remote surgeon to perform an endoscopic surgery.

The surgeon may provide input commands to the surgical robotic system, and one or more processors of the surgical robotic system can control system components in response to the input commands. For example, the surgeon may hold in her hand a user input device such as a joystick or a computer mouse that she manipulates to generate control signals to cause motion of the surgical robotic system components, e.g., an actuator, a surgical robotic arm, and/or a surgical tool of the robotic system.

SUMMARY

For a teleoperated surgical robotic system with an open display in which the user can view their surroundings (as compared to a periscope type display) there is the possibility that the surgeon is looking away from the screen but still holding the user input devices (UIDs) that control the robotic tools. This introduces a risk since the surgeon could move the UIDs and unintentionally move the tools while not focusing on the screen. The instant disclosure describes methods for determining whether the teleoperation mode should be paused or disengaged based on a gaze of the user. For example, the system includes an eye tracker attached to a three dimensional (3D) display which can detect if the surgeon is looking off screen and can pause teleoperation as soon as the surgeon is determined to be looking away. If additional conditions are met (such as moving the UIDs while looking away or looking away for longer than a predetermined time) teleoperation may be disengaged. If teleoperation is disengaged the system may be configured to require that the surgeon actively engage again after looking back at the screen. If teleoperation is only paused, the system may be configured to allow the surgeon to immediately take control of the tools once they look back at the screen, without any further action.

In some aspects, the method may include what are referred to herein as a gaze-off-screen operation and a gaze-teleop-interlock operation. The gaze-off-screen operation may determine if a user is looking off screen or not. The gaze-teleop-interlock may determine when teleoperation should be paused and when teleoperation should be disengaged in part, based on the outcome of the gaze-off-screen operation. For example, in the gaze-off-screen operation, the system determines if a user is looking at the screen or not based on gaze data collected by an eye tracker. Representatively, based on the data collected by the eye tracker, the gaze-off-screen operation determines the probability that the user is looking at the screen (and therefore teleoperation mode can continue or be engaged) or that the user is looking off screen (and therefore teleoperation mode should be paused or disengaged). Exemplary data and/or information that may be evaluated in the gaze-off-screen operation may include the following:

(1) If both eyes are invalid (e.g., not detected by the tracker) or if both are valid (e.g., detected by the tracker) but the distance between their calculated screen points is too large, the probability that the user may not be looking at the screen increases;

(2) If at least one eye is valid and inside (e.g., within the bounds of the display), this indicates that the tracker is certain that at least one eye is looking inside. The probability that the user is not looking at the screen decreases and/or is low, or said another way, the probability of the user looking at the screen is determined to be high;

(3) If both eyes are valid and outside or one valid and outside, this indicates that the tracker is certain that no eye is looking inside and at least one is looking outside. The probability of the user not looking at the screen increases and/or is high, or said another way, the probability that the user is looking at the screen decreases and/or is low.

In another embodiment, an exemplary gaze-off-screen operation may include the following:

(1) Determine if the gaze point is a fixation or a saccade (e.g., rapid movement between fixation points). This is done for the left and right gaze point;

(2) If at least one eye is fixating and inside, the probability of being on-screen increases.

(3) If at least one eye is fixating and outside, the probability of being off-screen increases.

(4) If both eyes are in a saccade, the probability of being off-screen increases.

Exemplary gaze-teleop-interlock scenarios for determining whether, based on the gaze-off-screen analysis, the teleoperation mode should be disengaged, paused and/or engaged are as follows: (1) If the user looks away for more than a blink or quick glance, pause teleoperation, and when the user looks back at the screen, s/he can immediately control the tools; (2) If the user looks away for a significant amount of time, or the user moves the teleoperation controllers (UID) a significant amount while looking away, disengage teleoperation mode. Once disengaged, the user will need to actively engage again to take control of the tools.

Representatively, in one aspect, the invention is directed to a method for disengaging a surgical instrument of a surgical robotic system. The method may include receiving a gaze input from an eye tracker that tracks a gaze of a user relative to a display associated with the surgical robotic system and determining, by one or more processors communicatively coupled to the eye tracker, whether the gaze input indicates the gaze of the user is outside or inside of the display. In response to determining the gaze input indicates the gaze of the user is outside of the display, the method determines an amount of time the gaze of the user is outside of the display. In response to determining the gaze of the user is outside of the display for less than a maximum amount of time, the method may pause the surgical robotic system from a teleoperation mode such that a user interface device of the surgical robotic system is prevented from controlling the surgical instrument until a gaze input indicating the gaze of the user is inside of the display is received. In addition, in response to determining the gaze of the user is outside of the display for more than the maximum amount of time, the method may include disengaging the surgical robotic system from the teleoperation mode such that the user interface device is prevented from controlling the surgical instrument until an active engagement input is received. In addition, determining the gaze input indicates the gaze of the user is outside of the display may include receiving a valid gaze input indicating that a gaze for both eyes of the user are detected by the eye tracker; and determining a distance between the gaze for both eyes is outside of a maximum distance associated with a size of the display. Still further, the aspect of determining the gaze input indicates the gaze of the user is outside of the display may include receiving an invalid gaze input indicating a gaze of at least one eye of the user is undetectable by the eye tracker; and determining a gaze path or a gaze location of the at least one eye is moving toward a border of the display. Moreover, the aspect of determining the gaze input indicates the gaze of the user is outside of the display may include receiving a head location input from a head tracker associated with the surgical robotic system; and determining, based on the head location input, a nose of the user is not facing the display or a face of the user is undetectable. In addition, determining the gaze of the user is inside the display may include receiving a valid gaze input indicating that a gaze of at least one eye of the user is detected by the eye tracker; and determining a location of the gaze is within the display. The method may further include receiving a movement input from the user interface device of the surgical robotic system; and in response to receiving the movement input when the surgical robotic system is paused, disengage the surgical robotic system. In some aspects, the active engagement input indicates a user is facing the display, a surgical chair is in a particular orientation, or the user interface devices is in a particular orientation. In some aspects, the maximum amount of time may be more than 100 milliseconds.

In another aspect, a surgical robotic system. The surgical robotic system may include a surgical instrument, a user console comprising a display, an eye tracker for tracking a gaze of a user with respect to the display, and a user interface device, and one or more processors communicatively coupled to the surgical instrument and the user console. The processor may be configured to: receive a gaze input from the eye tracker; determine whether the gaze of the user is outside or inside of the display based on the gaze input; and pause and/or disengage the surgical robotic system from a teleoperation mode when the user gaze is outside the display such that the user interface device is prevented from controlling the surgical instrument. The display may be an open display including a screen and a frame surrounding the screen. The user interface device may be a portable handheld user input device that is mechanically ungrounded with respect to the user console. The system may further include a head tracker, and determining whether the gaze of the user is outside or inside the display is based on a head location input from the head tracker. In addition, the gaze of the user may be determined to be outside of the display when a gaze for both eyes of the user are detected by the eye tracker; and a distance between the gaze for both eyes is outside of a maximum distance associated with a size of the display. In some aspects, the gaze of the user is determined to be outside of the display when a gaze of at least one eye of the user is undetectable by the eye tracker; and a gaze path or a gaze location of the at least one eye is moving toward a border of the display. In other aspects, the gaze of the user is determined to be outside of the display when a head location input from a head tracker associated with the surgical robotic system indicates a nose of the user is not facing the display or a face of the user is undetectable. Still further, the gaze of the user is determined to be inside the display when a gaze of at least one eye of the user is detected by the eye tracker; and a location of the gaze is within the display. In some aspects, the system further includes a user interface device motion sensor, and the surgical robotic system is paused and/or disengaged from a teleoperation mode when a motion of the user interface device greater than a maximum translation is detected. In some aspects, in response to determining the gaze of the user is outside of the display for less than a maximum amount of time, the surgical robotic system is paused from a teleoperation mode such that a user interface device of the surgical robotic system is prevented from controlling the surgical instrument until a gaze input indicating the gaze of the user is inside of the display is received. In some aspects, the maximum amount of time may be more than 100 milliseconds. In response to determining the gaze of the user is outside of the display for more than a maximum amount of time, the surgical robotic system may be disengaged from the teleoperation mode such that the user interface device is prevented from controlling the surgical instrument until an active engagement input is received.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Figure 1:
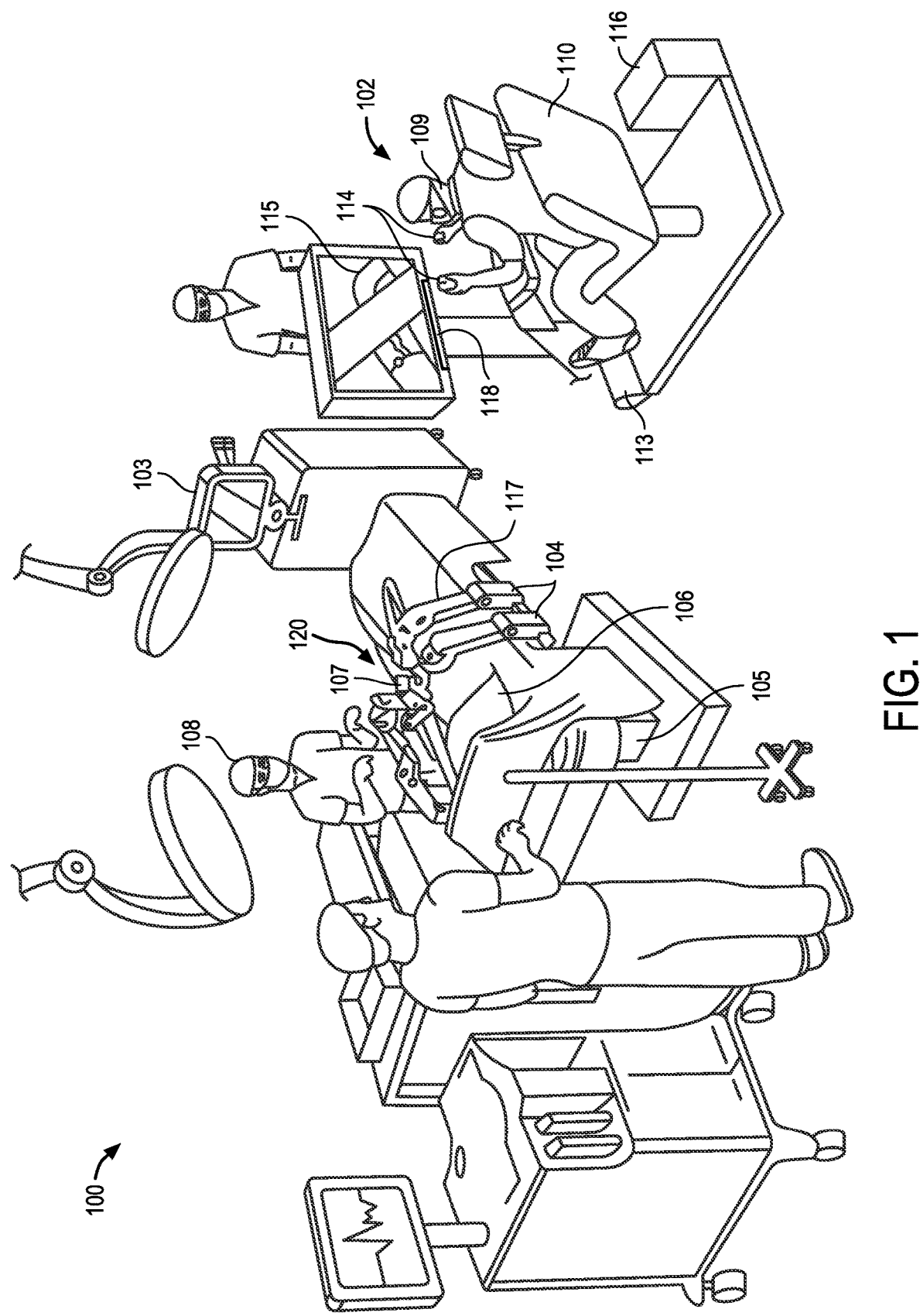
FIG. 1 is a pictorial view of an example surgical robotic system in an operating arena, in accordance with an embodiment.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation or teleoperation mode. The user console 102 may be located in the same operating room as the rest of the system 100, as shown in FIG. 1. In other environments however, the user console 102 may be located in an adjacent or nearby room, or it may be at a remote location, e.g., in a different building, city, or country. The user console 102 may comprise a seat 110, foot-operated controls 113, one or more handheld user input devices, UID 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104.)

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site.) Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console 102. The UID 114 can generate spatial state signals corresponding to movement of the UID 114, e.g., position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate, for example, a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm 104 that is at the left side of the patient. An actuator 117 may include one or more motors that are controlled so that they drive the rotation of a joint of the arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the platform 105 and the user console 102 may be through a control tower 103, which may translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. It will be appreciated that the operating room scene in FIG. 1 is illustrative and may not accurately represent certain medical practices.

In addition, in some aspects, surgical robotic system 100 may further include a tracking component 118 for tracking a characteristic of the user, for example, the remote operator 109. The tracked characteristic can, in turn, be used by the system 100 to automatically control an operation of the surgical robotic system. For example, during a teleoperation mode of the surgical robotic system 100, in which the user is controlling the surgical tool 107 using the UID 114, the user should be viewing the tool movement on display 115. In some cases, however, the user may look away from the display 115 (intentionally or unintentionally) while still holding the UID 114 and controlling the surgical tool 107. This introduces a risk since the user could move the UID 114 and, in turn, unintentionally move the tool 107 while not focused on the display 115. Surgical robotic system 100 may therefore further include a tracking component 118 that tracks a characteristic of the user that can be used to determine whether the user is focused on the display 115 and, in turn, intentionally operating the UID 114 and associated tool 107, or not focused on the display such that a teleoperation mode should be disengaged or the system should transition to a non-teleoperation mode. For example, in one aspect, the tracking component 118 may be an eye tracker that can detect if the user is looking away from, or otherwise outside of, the display, based on the gaze of the user. If it is determined that the user gaze is outside of the display, and therefore the user may be looking away from the display, the system may automatically pause the teleoperation mode so that the user is temporarily prevented from using the UID 114 to move the surgical tool 107. For example, teleoperation mode may be paused until the tracking component 118 detects that the gaze is inside of the display, and therefore the user is looking back at the display. In addition, the tracking component 118 may be used to detect additional characteristics of the user, that if detected in addition to detecting the user is looking away, will cause the surgical robotic system to disengage the teleoperation mode. For example, if it is determined the user gaze is outside of the display and it is further determined that the user gaze is outside of the display for more than a maximum amount of time, the system may automatically disengage teleoperation mode. In addition, if it is determined the gaze is outside the display and the UID 114 is moving, the system may automatically disengage teleoperation mode.

It should be understood that "pausing" a teleoperation mode, is intended to refer to a different system operation, with different consequences, than "disengaging" a teleoperation mode. In particular, pausing a teleoperation mode may be an operation that occurs when the system determines the user may be briefly looking away from the display (e.g., to reach another system component, readjust their position, etc.), but there is otherwise a high probability that the user is generally engaged and focused on the surgical operation or procedure. In this aspect, the system determines it is only necessary to temporarily prevent the UID 114 from controlling the tool 107, and teleoperation mode is paused, but is not disengaged or transitioned entirely out of a teleoperation mode. In addition, since the user is otherwise engaged with the system and there is little risk of an unintended action occurring, a relatively small input to the system may un-pause teleoperation mode. For example, if the input causing the system to pause teleoperation mode is a determination or detection that the user gaze is outside of the display for not more than a maximum period of time, the input required to un-pause teleoperation mode may be a determination or detection that the user gaze is once again inside the display.

"Disengaging" the teleoperation mode, on the other hand, is intended to refer to an operation which occurs when it is determined there is a high probability that the user is not engaged or focused on the surgical operation or procedure, therefore it is inappropriate to continue in teleoperation mode. Disengaging teleoperation mode is therefore a more permanent operation which prevents the UID 114 from controlling the tool 107 until an intentional action or sequence of actions which clearly indicate the user is now engaged and focused on the operation, and desires to re-engage teleoperation mode, occurs. For example, as previously discussed, teleoperation mode may be disengaged when the system determines that the user gaze is outside of the display for more than a maximum period of time, or outside of the display in combination with the detection of a movement of the UID. Such actions suggest a high probability that the user is not focused on the procedure at hand, and it may not be appropriate to continue in teleoperation mode. The system will therefore automatically disengage the teleoperation mode so that the UID 114 cannot control the tool 107. To re-engage teleoperation mode, an intentional action or sequence of actions clearly indicating the user is focused on controlling the system is necessary. For example, the action(s) indicating the user is focused on the operation may be that the user is facing the display, the user's chair is in a particular orientation, the UID is in a particular orientation, etc.

In addition, it is noted that the term "open display" is intended to refer to a display which is designed to allow the user to see outside of the display, for example with their peripheral vision, even when directly facing the display. In addition, in an open display, the user can be a distance from the display screen, or not directly in front of the display, and still view a surgical procedure on the display. Therefore, in an open display system as disclosed herein, the fact that the user may not be close to the display or have their face directly in front of the display, would not necessarily be interpreted to mean the user is distracted, or otherwise not paying sufficient attention to continue a surgical procedure. In the case of an open display, in which the user can turn their head and still see the display using their peripheral vision, it is therefore important that turning of the head slightly not be considered a characteristic that will automatically disengage the teleoperation mode. Rather, an open architecture or display surgical robotic system as disclosed herein will have some tolerance to such actions and allow the user to continue controlling a surgical tool. This is in contrast to a closed architecture system which includes, for example, a periscope with a completely immersive display that prevents the user from seeing outside of the display screen when they are facing the display and requires the user to be relatively close to the display screen. For example, in the case of a periscope, the user must have their face relatively close to, and facing, the display screen to use it to view the surgical procedure in progress. If the user pulls their head away from the display screen, or does not face the display screen, they can no longer see the display screen, therefore this would typically be interpreted to mean the user is distracted or not paying sufficient attention to continue a surgical procedure.

Figure 2:
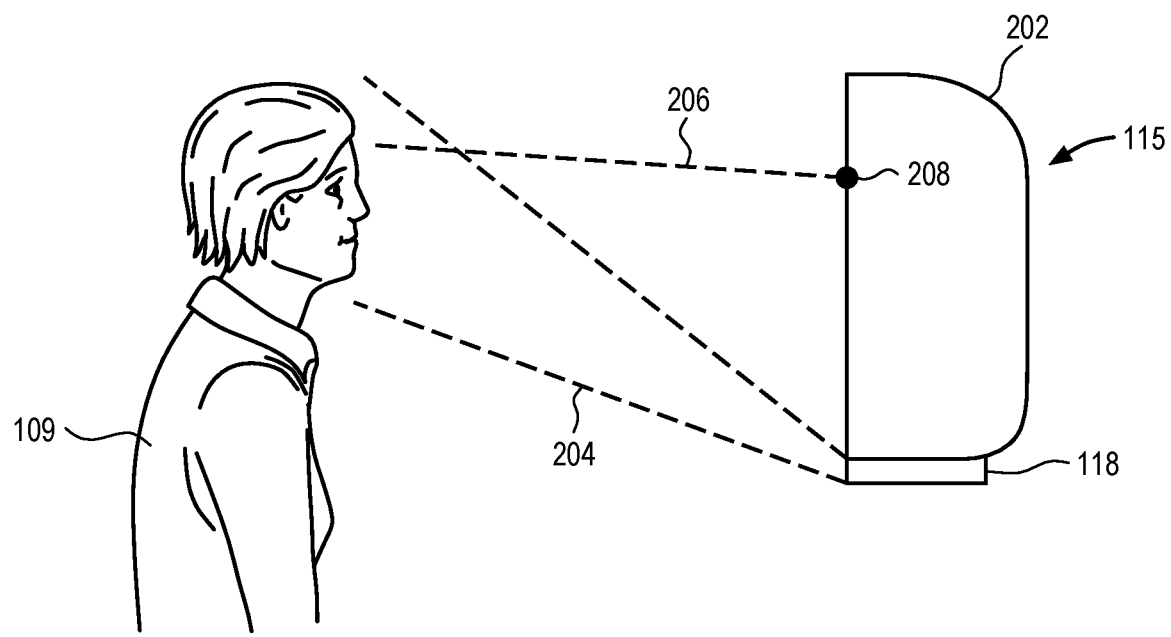
FIG. 2 is a pictorial view of a display and gaze tracker, in accordance with an embodiment.

Referring now to FIG. 2, FIG. 2 illustrates a side pictorial view of an exemplary display and tracking component. Representatively, display 115 may include a tracking component 118 coupled to the display 115 in such a manner that that it can track a characteristic of a user. For example, in one embodiment, tracking component 118 is an eye tracker that is operable to track a gaze of a user relative to display 115. In this aspect, tracking component 118 may be attached to, or integrated within, any portion of display 115 suitable for tracking a gaze of user 109. For example, tracking component 118 may be attached to a housing 202 of display 115, for example, a top wall, a bottom wall, or a side wall of housing 202, or integrated within a screen (not shown) mounted within the housing 202 of display 115. The tracking component 118 may include one or more projector(s) and camera(s) which face the user and can be used to track a gaze of a user. Representatively, the projector(s) may create a pattern of near-infrared light on the eyes of the user, and the camera(s) may take images of the user's eyes and the pattern. The tracking component 118 may further be programmed to use this information (e.g., execute machine learning, image processing and/or mathematical algorithms) to determine where the user is looking based on a position of each of the user's eyes and/or gaze point or location relative to one another, and display 115. For example, when the user 109 is positioned in front of display 115 as shown in FIG. 2, the tracking component 118 may be configured to create a pattern of near-infrared light on the eyes of the user and take images of the user's eyes and the pattern when the user's head is within a predetermine sensing range 204 of tracker 118. This information may, in turn, be used by a surgical robotic system processing component to determine whether the gaze 206 of the user 109 is at a gaze point 208 inside or outside of display 115, the user is looking toward or away from display 115, and whether to pause or disengage a teleoperation mode.

Representatively, in one aspect, the surgical robotic system implements a two-fold process for determining whether teleoperation mode should be paused or disengaged, based on the user's gaze. For example, the process may generally include a first sequence of operations used to determine if the user is looking toward or away from the display, also referred to in some embodiments as a gaze-off-screen operation. The process may further include a second sequence of operations used to determine when teleoperation mode should be paused and when teleoperation should be disengaged, based in part, on the outcome of the gaze-off-screen operation and the probability that the user is looking on/off display. The second sequence of operations may be referred to, in some embodiments, as a gaze-teleop-interlock operation because it may include one or more interlocks (e.g., conditions to determine if the user is focused on teleoperation) that may be considered when pausing or disengaging teleoperation mode.

Referring now in more detail to the gaze-off-screen operation, this operation may be used to determine a probability or likelihood that the user is looking at the display or is looking away from the display, by evaluating the gaze data collected by the eye tracker. It is further noted that the gaze-off-screen operation may be configured to discard blinks, and work for different users with, for example, different eye anatomy, no glasses, glasses, and/or contacts. The data collected by the eye tracker during this operation may be considered "valid", meaning the eye(s) are detected by the eye tracker, or "invalid", meaning the eye(s) are not detected by the eye tracker. For example, the eye tracker is programmed to detect the user gaze and/or gaze point within a predetermined sensing or gaze range, which may, for example, be determined based on a size of the display (with some tolerance range outside of the display). When the eye tracker cannot recognize or detect the gaze or pupil of one or both of the user's eyes within this predetermined sensing or gaze range, it generates an invalid signal. For example, when the user's head is turned such that one or both eyes of the user are at an angle to the display or the user is blinking, the eye tracker may not be able to recognized or detect the pupil or gaze of the user, and generate an invalid signal. In addition, the eye tracker may generate an invalid signal if both eyes are detected, but the gaze point between the eyes is unusually large or otherwise inconsistent with a typical user gaze. A valid signal, on the other hand, may be generated by the eye tracker when the eye tracker can detect one or both eyes, and/or the gaze point between both eyes is normal or otherwise consistent with a typical user gaze.

A probability or likelihood that the user gaze is on screen or off screen is then determined based on the received valid and/or invalid signals. For example, if the eye tracker determines that both eyes are invalid, or both eyes are valid, but the distance between calculated screen points of the corresponding gaze points is too large, this suggests a blink, the tracker is unable to see the eyes or inconsistencies for both eyes. In such cases, the probability the gaze is off-screen increases and the probability the gaze is on-screen decreases. In addition, if at least one eye is valid, and the gaze is inside the display, the probability the gaze is on-screen increases and the probability the gaze is off-screen decreases. Moreover, if two eyes are valid, and the gaze for both eyes are inside the display, the gaze-off-screen operation determines the gaze is on-screen and the probability the gaze is on-screen increases even more. On the other hand, if both eyes are valid and outside the display, or one is valid and outside the display, this suggests both eyes are looking outside the display or at least one eye is looking outside the display, and therefore the probability the gaze is off-screen is high.

In addition, to avoid false positives due to, for example, gaze loss from blinking, squinting or inaccurate gaze data, the gaze-off-screen operation may further consider the amount of time an invalid signal is detected, the gaze point or gaze path detected prior to the invalid signal, a location and/or orientation of the head and/or face, and/or track eye ball locations. Based on all the data collected, the probability or likelihood the user is looking off-screen versus the probability the user is looking on-screen is weighed to evaluate the risks of continuing teleoperation mode and need for further action (e.g., pause or disengage teleoperation mode).

In particular, the gaze-teleop-interlock operation, based at least in part on the outcome of the gaze-off-screen operation, may determine whether to pause or disengage teleoperation. For example, the gaze on-screen and gaze-off screen probabilities may be weighed against one another as the data is received and used to evaluate whether the user is looking toward the display or away from the display, and in turn, whether teleoperation should be paused (e.g., probability user is looking toward the display>probability user is looking away from the display) or disengaged (e.g., probability user is looking away from the display>probability user is looking toward the display) by the gaze-teleop-interlock operation. Moreover, in an open architecture system as contemplated herein, interactions between the user and staff are expected and the system should support this behavior to some extent. In order to do that, when the gaze-off-screen operation determines the user is looking off screen, the gaze-teleop-interlock operation determines whether the user is looking away for more than a blink or a quick glance, and if so, causes the system to pause the teleoperation mode. When it is determined that he user is looking back at the display (e.g., a valid signal is detected), teleoperation is un-paused, and the user can immediately control the tools. On the other hand, if the user looks away for a significant amount of time, or the user moves the UID a significant amount while looking away, the gaze-teleop-interlock operation determines it is not appropriate for the user to continue operating the tool and causes the system to disengage teleoperation.

Exemplary processes for determining if the user gaze is inside or outside of the display 115, the user is looking toward or away from the display and/or whether to pause or disengage a teleoperation mode, will now be discussed in more detail in reference to FIG. 3-FIG. 6.

Figure 3:
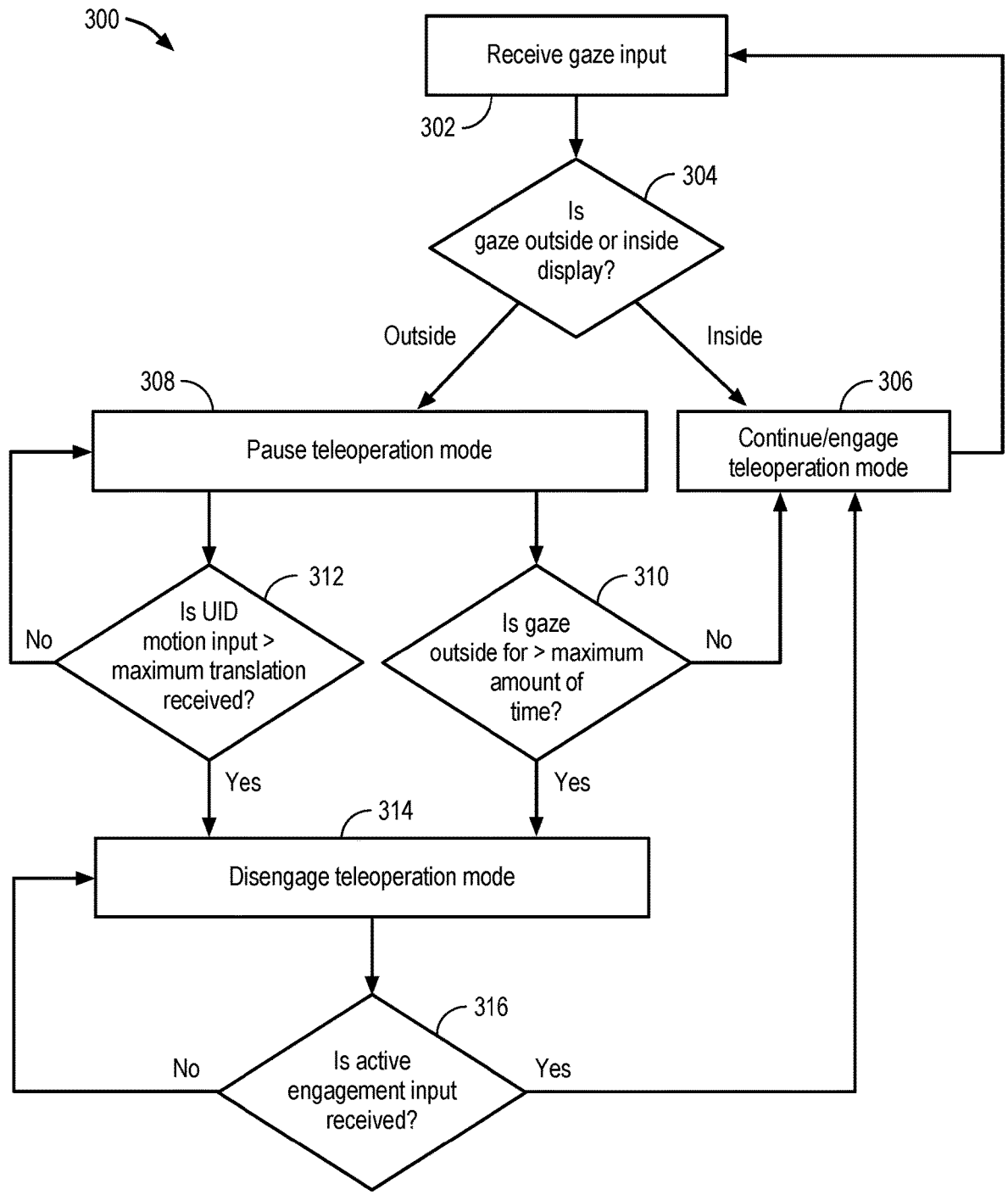
FIG. 3 is a block diagram of an exemplary operation for disengaging a teleoperation mode based on a user gaze, in accordance with an embodiment.

Representatively, referring now to FIG. 3, FIG. 3 illustrates a block diagram of an exemplary process for disengaging a teleoperation mode based on a user gaze. In particular, process 300 may include an initial operation of receiving a gaze input (block 302). The gaze input may be the user gaze, gaze point and/or gaze location information detected by the tracking component 118, more specifically an eye tracking component, as previously discussed. This information is then used to determine whether the user gaze is outside or inside of the display (block 304). The process for determining whether the user gaze is outside or inside the display based on this information will be discussed in more detail in reference to FIG. 4.

Returning now to FIG. 3, if it is determined that the user gaze is inside the display, teleoperation mode continues (block 306). If, however, it is determined at operation 304 that the user gaze is outside of the display, teleoperation mode is paused (block 308). As previously discussed, pausing of the teleoperation mode temporarily prevents the UID 114 from controlling the tool 107 until, for example, a reverse operation is detected. In this aspect, tracking component 118 may continue to check for a user gaze, for example, every 10-20 milliseconds, to determine whether the user gaze is outside of the display for more than a maximum amount of time (block 310). If it is not outside the display for more than the maximum amount of time, in other words a user gaze inside of the display is detected before the maximum amount of time has passed, process 300 returns to operation 306 and teleoperation mode will be automatically un-paused so that the user can continue teleoperation mode and control the instrument using the UID. The maximum amount of time may be, for example, the amount of time it takes a person to blink. For example, the average blink may last from 100 milliseconds to 300 milliseconds, therefore the maximum amount of time may be 100 milliseconds, 200 milliseconds, 300 milliseconds. In still further embodiments, the maximum amount of time may correspond to an amount of time that is determined to be inappropriate to continue with operation of the system. For example, the maximum amount of time may be about 5 seconds or more.

If, on the other hand, the user gaze is determined to be outside of the display for more than the maximum amount of time (e.g., more than 100 milliseconds, more than 200 milliseconds, more than 300 milliseconds or more than 5 seconds), teleoperation mode may be disengaged (block 314). In addition, in some cases, process 300 may further detect a UID motion input and use the motion input, in combination with the gaze input, to determine whether to disengage teleoperation mode. Representatively, process 300 may include the further operation of detecting a motion of the UID using a UID motion sensor associated with the system and determining whether the motion input is greater than a maximum translation (block 312). If this UID motion input is not greater than a maximum translation, teleoperation mode may remain paused. If the UID motion input is greater than a maximum translation, teleoperation mode is disengaged (block 314). The "maximum translation" may refer to, for example, a maximum acceptable range of motion of the UID which can occur when the user is not looking at a display. For example, a relatively small movement of the UID such as would occur when the user is adjusting their hand and/or wrist position while holding the UID would be considered an acceptable range. Alternatively, a relatively large movement of the UID such as would occur when the user engages in an unintentional movement of the UID or has dropped the UID would be greater than the maximum acceptable range of motion of the UID and cause the system to disengage teleoperation. Once disengaged from teleoperation mode, process 300 determines whether an active engagement input is received (block 316). If an active engagement input is received, process 300 will return to operation 306 and teleoperation mode may be re-engaged so that teleoperation mode can continue. If an active engagement input is not received, process 300 will remain disengaged from teleoperation mode until the active engagement input is received. As previously discussed, an active engagement input may be an intentional action or sequence of actions that indicate a desire by the user to re-engage teleoperation mode (e.g., control instrument 107 using UID 114). For example, the action(s) indicating the user is focused on the operation may be that the user is facing the display, the user's chair is in a particular orientation, the UID is in a particular orientation, etc.

Figure 4:
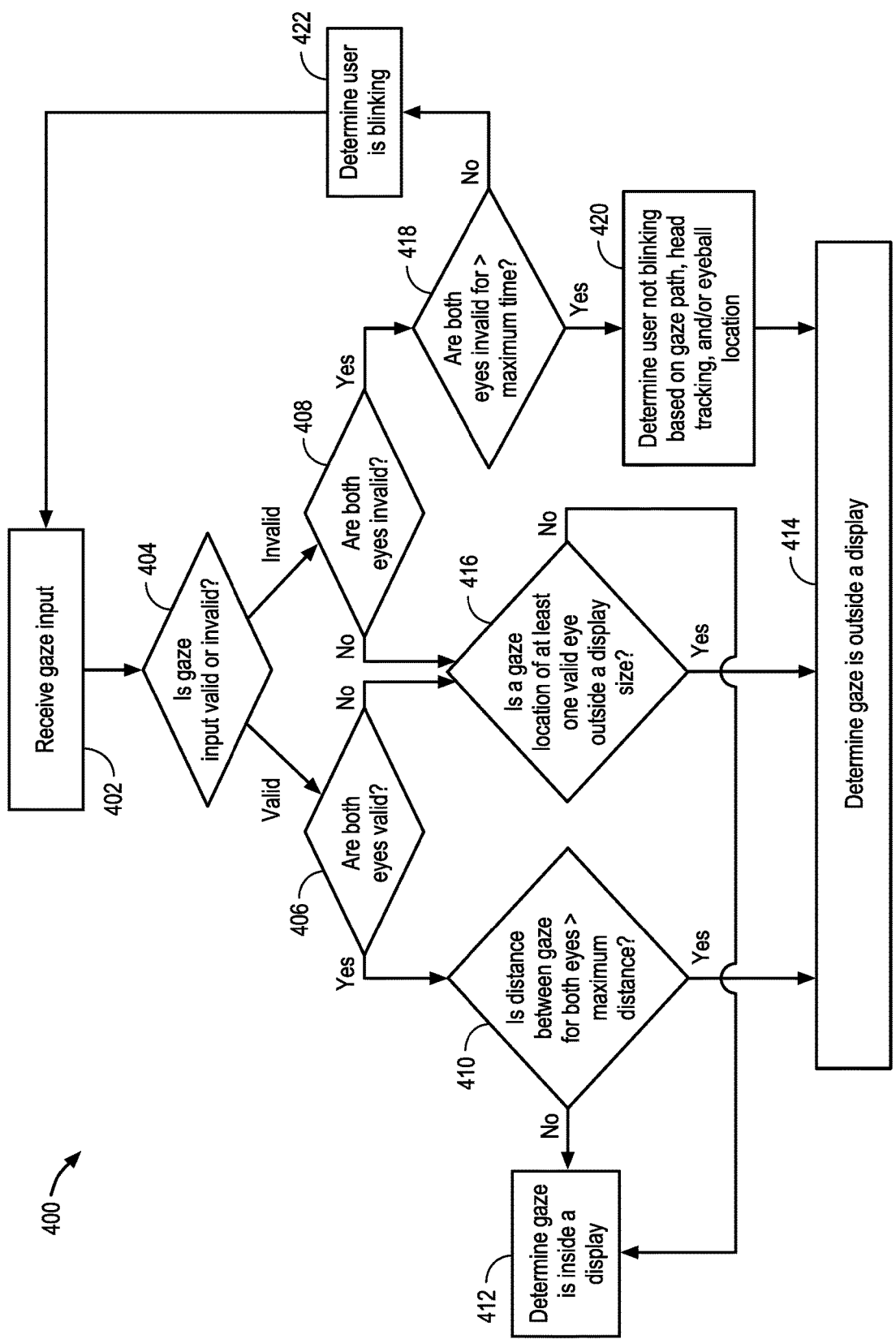
FIG. 4 is a block diagram of an exemplary operation for determining whether a user gaze is outside a display, in accordance with an embodiment.

FIG. 4 is a block diagram of an exemplary operation for determining whether a user gaze is outside a display, in accordance with an embodiment. Process 400 may include an initial operation of receiving a gaze input (block 402), which is similar to operation block 302 of process 300. The remaining operations of process 400 are then used to determine whether the gaze of a user is outside or inside a display (e.g., operation block 304 of process 300). Representatively, once the gaze input is received (block 402), it is determined whether the gaze input is valid or invalid (block 404), as previously discussed.

Figure 5:
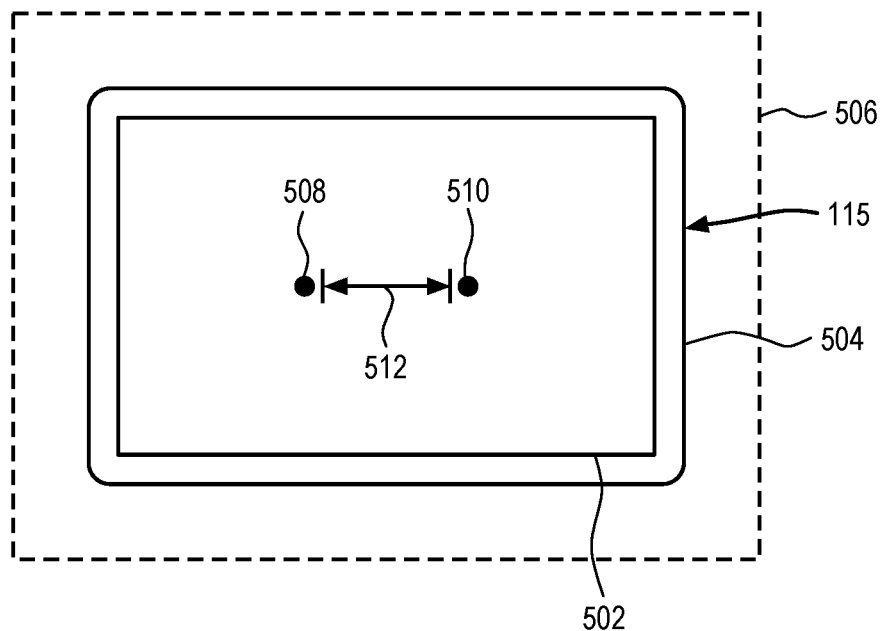
FIG. 5 is a pictorial view of an exemplary operation for determining whether a user gaze is outside a display, in accordance with an embodiment.

If a valid gaze input is received, process 400 continues to operation 406 to determine whether both eyes are valid. If both eyes are valid, process 400 continues to operation 410 where a distance between a gaze point for both eyes is analyzed to determine whether it is greater than a maximum distance. The maximum distance may be a distance between a gaze point of each eye of the user which is considered within the range of a normal user gaze looking at the display. An exemplary maximum distance between a gaze point of each eye is illustrated in FIG. 5. Representatively, FIG. 5 illustrates a display 115 including a screen 502 and a frame 504 around the screen 502. A gaze point or location of a left eye is illustrated by point 508 and a gaze point or location of a right eye is illustrated by point 510. A measurement of the distance between gaze points 508, 510 is illustrated by line 512. If this distance 512 between a gaze point for both eyes is not greater than the maximum distance, the user gaze is considered consistent with a user looking at the display, and it is determined that the user gaze is inside the display (block 412). On the other hand, if the distance 512 between the gaze point for both eyes is greater than the maximum distance, the gaze is not consistent with a user looking at the display, and it is determined that the user gaze is outside the display (block 414).

If both eyes are not invalid (e.g., one eye is invalid and one eye is valid), operation 400 continues to operation block 416 where it is determined whether a gaze point or location of at least one valid eye is outside of the size of the display. For example, as previously discussed in reference to FIG. 5, display 115 may include screen 502 and frame 504 around the screen 502, such that the size of the display corresponds to an area or region at least as big as the frame surrounding the screen. In some cases, the size of the display may extend a distance outside of the frame which accounts for the peripheral vision of the user. The size of the display including this tolerance range outside of the frame is illustrated by dashed line 506. In other words, the gaze point or location could be slightly outside of the frame (e.g., within range 506) but a peripheral vision of the user would allow the user to still see the screen, therefore the user gaze point or gaze location, and in turn the user gaze, will still be considered inside the size of the display (or inside the display). Alternatively, if the gaze point or gaze location is outside of the range 506, the gaze point or gaze location, and in turn the user gaze, is considered outside of the size of the display (or outside of the display). If the gaze location of the at least one valid eye is not determined to be outside of the size of display 506, process 400 continues to operation block 412 and determines the user gaze is inside of the display. If, however, the gaze point or location of one valid eye is outside of the size of display, process determines the user gaze is outside of the display at operation block 414.

If, on the other hand, an invalid gaze input is received at operation block 404, process 400 continues to operation block 408 to determine whether both eyes are invalid. If both eyes are not invalid (e.g., one eye is invalid and one eye is valid), operation 400 continues to operation block 416 where it is determined whether a user gaze, gaze point or location of at least one valid eye is outside of the size of the display as previously discussed.

If, on the other hand, it is determined at operation block 408 that both eyes are invalid, process 400 continues to operation block 418 where it is determined whether both eyes are invalid for more than a maximum amount of time. The maximum amount of time may be, for example, the amount of time that an average blink lasts. For example, the maximum amount of time may be 100 milliseconds, 200 milliseconds or 300 milliseconds. In some cases, the maximum amount of time may be around 5 seconds. If both eyes are not invalid for more than the maximum amount of time (e.g., a valid input is received in 100 milliseconds, 200 milliseconds or 300 milliseconds, or less), process determines the user was blinking (block 422). Blinking is treated as though the user is still looking at the screen, therefore process 400 returns to operation block 402 and continues the gaze input analysis.

If, on the other hand, both eyes are invalid for more than the maximum amount of time (e.g., more than 100 milliseconds, more than 200 milliseconds, or more than 300 milliseconds), the possibility that the invalid signal is due to, for example, the user blinking, squinting, inaccurate data, etc. is unlikely. Instead, it is more likely the case that the user is looking away from the display. To confirm blinking can be ruled out, process 400 may further evaluate the last gaze location or gaze path, head location/orientation and/or eyeball location of the user at operation block 420.

Figure 6:
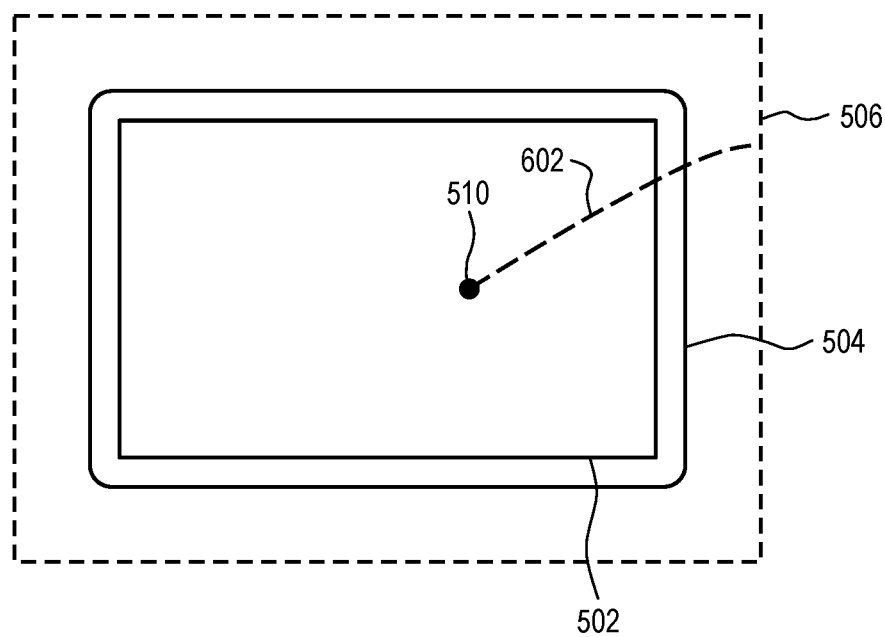
FIG. 6 is a pictorial view of an exemplary operation for determining whether a user gaze is outside a display, in accordance with an embodiment.

Representatively, FIG. 6 illustrates one exemplary operation for evaluating the last gaze point or location, or gaze path of the user. The last gaze point or location is illustrated in FIG. 6 as point 510 and the gaze path is illustrated as dashed line 602. If the gaze point 510 and gaze path 602 are detected by the eye tracker as moving toward the border of the display 506 prior to receiving the invalid signal, this suggests the user is turning their head away from the display and can be used to rule out blinking, squinting and/or inaccurate data. Alternatively, if the gaze point 510 is fixed prior to receiving the invalid signal, this suggests the user is not turning their head away from the display and there is still a possibility that the invalid signal is due to the user blinking, squinting and/or inaccurate data.

In some cases, for example where it is not entirely clear from the gaze location/path information whether the invalid input is due to the user blinking or looking away from the display, a head location/orientation input may further be received and considered in operation 420. The head location input may be received, for example, from a tracking component that tracks a head location and/or face of the user. For example, tracking component 118 may be, or may further include, a head tracker, with similar tracking components (e.g., projector(s) and camera(s)) which can be used to detect when the user's nose is pointing toward the display. The tracker can further track the user's face and indicate when the ace is no longer visible. For example, if a head location input indicating the user's face is no longer visible or not aligned with the display (e.g., the user's nose is not facing the display) is received, process 400 confirms blinking may be ruled out. Still further, in some cases, the tracking component can track the eyeball location instead of, or in addition to, head tracking, and be used to distinguish between looking away from the display and blinking. For example, the tracking component can track whether the last detected eyeball location was fixed, or was moving toward the border of the display 506, to distinguish between blinking and looking away from the display.

Operation 420, however, is optional therefore in some cases, operation 420 is omitted and process 400 proceeds from operation block 418 to operation block 414 where it is concluded that the gaze is outside of the display.

Figure 7:
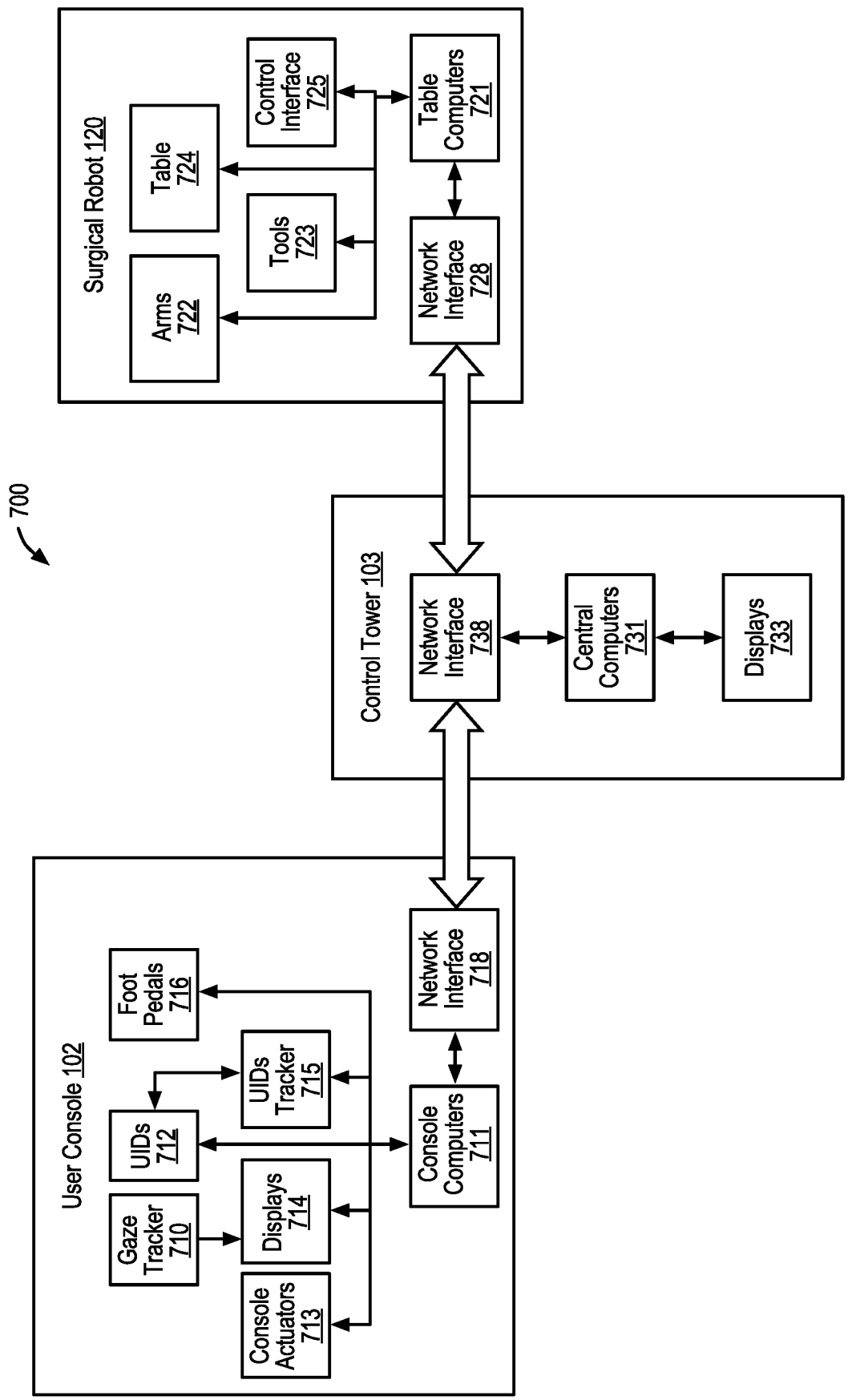
FIG. 7 is a block diagram of a computer portion of a surgical robotic system, in accordance with an embodiment.

Referring now to FIG. 7, FIG. 7 is a block diagram of a computer portion of a surgical robotic system, which is operable to implement the previously discussed operations, in accordance with an embodiment. The exemplary surgical robotic system 700 may include a user console 102, a control tower 103, and a surgical robot 120. The surgical robotic system 700 may include other or additional hardware components; thus, the diagram is provided by way of example and not a limitation to the system architecture.

As described above, the user console 102 may include console computers 711, one or more UIDs 712, console actuators 713, displays 714, a UID tracker 715, foot pedals 716, and a network interface 728. A user or surgeon sitting at the user console 102 can adjust ergonomic settings of the user console 102 manually, or the settings can be automatically adjusted according to user profile or preference. The manual and automatic adjustments may be achieved through driving the console actuators 713 based on user input or stored configurations by the console computers 711. The user may perform robot-assisted surgeries by controlling the surgical robot 120 using one or more master UIDs 712 and foot pedals 716. Positions and orientations of the UIDs 712 are continuously tracked by the UID tracker 715, and status changes are recorded by the console computers 711 as user input and dispatched to the control tower 103 via the network interface 718. Real-time surgical video of patient anatomy, instrumentation, and relevant software apps can be presented to the user on the high resolution 3D displays 714 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly-adjustable seat for surgeons and master UIDs tracked through electromagnetic or optical trackers are included at the user console 102 for improved ergonomics.

In addition, as previously discussed, user console may include a tracking component for tracking a characteristic of a user, which can in turn be used to prevent accidental tool motion, for example, by pausing or disengaging teleoperation when the user's gaze is not engaged in the surgical site on the open display for over a predetermined period of time. Representatively, user console 102 may include a gaze tracker 710 that tracks a gaze of the user to determine whether to pause or disengage the teleoperation mode, as previously discussed in reference to FIG. 3 and FIG. 4. In addition, gaze tracker 710 may include a head tracking, eyeball tracking and/or surgical component tracking mechanism that can further be used to determine whether to pause or disengage the teleoperation mode as previously discussed.

The control tower 103 can be a mobile point-of-care cart housing touchscreen displays, computers that control the surgeon's robotically-assisted manipulation of instruments, safety systems, graphical user interface (GUI), light source, and video and graphics computers. As shown in FIG. 7, the control tower 103 may include central computers 731 including at least a visualization computer, a control computer, and an auxiliary computer, various displays 733 including a team display and a nurse display, and a network interface 728 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services.

The surgical robot 120 may include an articulated operating table 724 with a plurality of integrated arms 722 that can be positioned over the target patient anatomy. A suite of compatible tools 723 can be attached to or detached from the distal ends of the arms 722, enabling the surgeon to perform various surgical procedures. The surgical robot 120 may also comprise control interface 725 for manual control of the arms 722, table 724, and tools 723. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 722 includes four arms mounted on both sides of the operating table 724, with two arms on each side. For certain surgical procedures, an arm mounted on one side of the table can be positioned on the other side of the table by stretching out and crossing over under the table and arms mounted on the other side, resulting in a total of three arms positioned on the same side of the table 724. The surgical tool can also comprise table computers 721 and a network interface 728, which can place the surgical robot 120 in communication with the control tower 103.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A method for disengaging a surgical instrument of a surgical robotic system, the method comprising:
   receiving a gaze input from an eye tracker that tracks a gaze of a user relative to a display associated with the surgical robotic system;
   determining, by one or more processors communicatively coupled to the eye tracker, whether the gaze input indicates the gaze of the user is outside or inside of the display;
   in response to determining the gaze input indicates the gaze of the user is outside of the display, determining whether a movement of an interface device of the surgical robotic system detected by a motion sensor is less than or greater than a maximum translation;
   in response to determining the gaze of the user is outside of the display and (1) the movement of the interface device is less than the maximum translation, pause the surgical robotic system from a teleoperation mode, or (2) the movement of the interface device is greater than the maximum translation, disengage the surgical robotic system from the teleoperation mode such that the interface device is prevented from controlling the surgical instrument.

2. The method of claim 1 wherein determining the gaze input indicates the gaze of the user is outside of the display comprises:
   receiving a valid gaze input indicating that a gaze for both eyes of the user are detected by the eye tracker; and
   determining a distance between the gaze for both eyes is outside of a maximum distance associated with a size of the display.

3. The method of claim 1 wherein determining the gaze input indicates the gaze of the user is outside of the display comprises:
   receiving an invalid gaze input indicating a gaze of at least one eye of the user is undetectable by the eye tracker; and
   determining a gaze path or a gaze location of the at least one eye is moving toward a border of the display.

4. The method of claim 1 wherein determining the gaze input indicates the gaze of the user is outside of the display comprises:
   receiving a head location input from a head tracker associated with the surgical robotic system; and
   determining, based on the head location input, a nose of the user is not facing the display or a face of the user is undetectable.

5. The method of claim 1 wherein determining the gaze of the user is inside the display comprises:
   receiving a valid gaze input indicating that a gaze of at least one eye of the user is detected by the eye tracker; and
   determining a location of the gaze is within the display.

6. The method of claim 1:
   wherein the surgical robotic system is paused until a gaze input indicating the gaze of the user is inside of the display is received.

7. The method of claim 1 wherein the surgical robotic system is disengaged from the teleoperation mode until an active engagement input is received, and the active engagement input indicates a user is facing the display, a surgical chair is in a particular orientation, or the user interface devices is in a particular orientation.

8. The method of claim 1 further comprising determining whether the gaze of the user is outside of the display for greater than a maximum amount of time, and wherein the maximum amount of time is more than 100 milliseconds.

9. A surgical robotic system, comprising:
   a surgical instrument;
   a user console comprising a display, an eye tracker for tracking a gaze of a user with respect to the display, a motion sensor, and a user interface device; and
   one or more processors communicatively coupled to the surgical instrument and the user console, the processors configured to:
     receive a gaze input and a motion input from the eye tracker;
     determine whether the gaze of the user is outside or inside of the display based on the gaze input;

determine whether a movement of an interface device of the surgical robotic system detected by the motion sensor is less than or greater than a maximum translation; and pause and/or disengage the surgical robotic system from a teleoperation mode when the user gaze is outside the display and the movement of the interface device is greater than the maximum translation such that the interface device is prevented from controlling the surgical instrument.

10. The surgical robotic system of claim 9 wherein the display is an open display comprising a screen and a frame surrounding the screen.

11. The surgical robotic system of claim 9 wherein the user interface device is a portable handheld user input device that is mechanically ungrounded with respect to the user console.

12. The surgical robotic system of claim 9 further comprising a head tracker, and wherein determining whether the gaze of the user is outside or inside the display is based on a head location input from the head tracker.

13. The surgical robotic system of claim 9 wherein the gaze of the user is determined to be outside of the display when a gaze for both eyes of the user are detected by the eye tracker; and a distance between the gaze for both eyes is outside of a maximum distance associated with a size of the display.

14. The surgical robotic system of claim 9 wherein the gaze of the user is determined to be outside of the display when a gaze of at least one eye of the user is undetectable by the eye tracker; and a gaze path or a gaze location of the at least one eye is moving toward a border of the display.

15. The surgical robotic system of claim 9 wherein the gaze of the user is determined to be outside of the display when a head location input from a head tracker associated with the surgical robotic system indicates a nose of the user is not facing the display or a face of the user is undetectable.

16. The surgical robotic system of claim 9 wherein the gaze of the user is determined to be inside the display when a gaze of at least one eye of the user is detected by the eye tracker; and a location of the gaze is within the display.

17. The surgical robotic system of claim 9 wherein in response to determining the gaze of the user is outside of the display for less than a maximum amount of time, the surgical robotic system is paused from a teleoperation mode such that a user interface device of the surgical robotic system is prevented from controlling the surgical instrument until a gaze input indicating the gaze of the user is inside of the display is received.

18. The surgical robotic system of claim 17 wherein the maximum amount of time is more than 100 milliseconds.

19. The surgical robotic system of claim 9 wherein in response to determining the gaze of the user is outside of the display for more than a maximum amount of time, the surgical robotic system is disengaged from the teleoperation mode such that the user interface device is prevented from controlling the surgical instrument until an active engagement input is received.

* * * * *